US010155059B2

(12) United States Patent
Eastcott et al.

(10) Patent No.: US 10,155,059 B2
(45) Date of Patent: Dec. 18, 2018

(54) VOLATILE MATERIAL DISPENSER (71) Applicant: Personal Care Products, LLC, Troy, MI (US)

(72) Inventors: Jason R. Eastcott, Howell, MI (US); Sheng Zhou, Changzhou (CN)

(73) Assignee: Personal Care Products, LLC, Troy, MI (US)

( * ) Notice: Subject to any disclaimer, the term of this patent is extended or adjusted under 35 U.S.C. 154(b) by 325 days.

(21) Appl. No.: 14/640,170

(22) Filed: Mar. 6, 2015

(65) Prior Publication Data
US 2016/0256586 A1  Sep. 8, 2016

(51) Int. Cl.
*A61L 9/03* (2006.01)
*A01M 1/20* (2006.01)

(52) U.S. Cl.
CPC ........... *A61L 9/037* (2013.01); *A01M 1/2077* (2013.01)

(58) Field of Classification Search
CPC . A61L 9/037; A61L 9/015; A61L 3/02; A61L 9/03; A61L 9/12; A01M 1/2077; A01M 1/20; A01M 1/2022; A01M 1/2061; A01M 1/2083
USPC ................ 392/386, 390, 391, 392, 394, 396
See application file for complete search history.

(56) References Cited

U.S. PATENT DOCUMENTS

| 5,788,155 | A | 8/1998 | Martin et al. |
| 6,278,840 | B1* | 8/2001 | Basaganas Millan ....................... A01M 1/2077 261/DIG. 65 |
| 6,569,387 | B1 | 5/2003 | Furner et al. |
| 6,766,773 | B2 | 7/2004 | Wolpert et al. |
| 6,859,615 | B2 | 2/2005 | Yip et al. |
| 7,389,943 | B2 | 6/2008 | Jaworski |
| 8,170,405 | B2 | 5/2012 | Harris |
| 8,320,751 | B2 | 11/2012 | Porchia et al. |
| 2005/0194344 | A1 | 9/2005 | Heater |
| 2006/0153744 | A1* | 7/2006 | Thompson ............. A61L 9/035 422/122 |
| 2007/0295746 | A1* | 12/2007 | Gapp ..................... G07F 11/04 221/304 |
| 2011/0139884 | A1 | 6/2011 | Gasper et al. |
| 2011/0253801 | A1 | 10/2011 | Buschmann |
| 2012/0012667 | A1 | 1/2012 | Gasper et al. |
| 2012/0012668 | A1 | 1/2012 | Belongia |
| 2012/0018453 | A1 | 1/2012 | Westphal |
| 2012/0111966 | A1 | 5/2012 | Barlow et al. |

(Continued)

FOREIGN PATENT DOCUMENTS

WO    2012175984    12/2012

*Primary Examiner* — Brian Jennison
(74) *Attorney, Agent, or Firm* — Clark Hill PLC (57) ABSTRACT

The invention provides a volatile material dispenser having a housing and an implement which is operatively associated with the housing. The implement is configured to be movable between a first position and a second position, wherein the implement is configured to retain a first refill when the implement is in the first position, and wherein the implement is configured to retain a second refill when the implement is in the second position, and wherein the first and second refills have different features. The dispenser may include a heater and a visual indicating system. The invention further provides a method of converting the volatile material dispenser for use between the first refill and the second refill, and a method of retaining one of the refills in the volatile material dispenser.

20 Claims, 10 Drawing Sheets

(56) References Cited

U.S. PATENT DOCUMENTS

2012/0253801 A1 10/2012 Santos-Lang et al.
2012/0312893 A1 12/2012 Santini et al.
2014/0037273 A1* 2/2014 Jaworski ............... A61L 9/037
                                                392/390

* cited by examiner

VOLATILE MATERIAL DISPENSER

FIELD OF THE INVENTION

This invention is generally directed to a volatile material dispenser for dispensing volatile materials containing a chemical active such as an insecticide, a fragrance, an odor eliminator, or the like. In particular, this invention is directed to a volatile material dispenser, namely a plug-in scented oil dispenser, for dispensing volatile materials containing a chemical active such as an insecticide, a fragrance, an odor eliminator, or the like, where the volatile material dispenser is adjustable such that it can receive and retain refills having different features.

BACKGROUND OF THE INVENTION

Multiple different volatile material dispensers are commercially sold and generally include a housing and a refill that is inserted into the housing. The refill generally includes a container portion for holding a volatile material therein. In some dispensers, the volatile material is passively emitted therefrom. In other dispensers, a diffusion element is utilized to facilitate the dispensing of the volatile material. Regardless of the manner in which the volatile material is emitted, once the volatile material has been expended from the refill, the refill is removed by a user and replaced with a new refill.

One type of commercial volatile material dispenser, referred to herein as a plug-in scented oil dispenser, includes a housing and a heater disposed within the housing. A refill for use with a plug-in scented oil dispenser generally includes a container portion having a bottom end and a top end, wherein the container portion terminates in a neck portion at the top end. A volatile material is disposed within the container portion and a wick is in contact with the volatile material and extends out of the refill through the neck portion. A plug or other connector generally positions and retains the wick within the neck. Upon insertion of the refill into the dispenser, at least a portion of the wick is disposed adjacent the heater such that volatile material that moves through the wick is volatilized by the heater.

One of the disadvantages of many of the volatile material dispensers and refills therefore, such as the plug-in scented oil dispenser discussed above, is that each refill has features that are unique or complementary to the particular housing of the dispenser for which it is sold. Still further, each type of dispenser is adapted to accept only a single type of refill having features unique or complementary to that dispenser. For example, all plug-in scented oil dispensers sold by Reckitt Benckiser ("Reckitt") of England generally only accept refills sold by Reckitt under its Air Wick® brand and such refills are designed to only fit with Reckitt plug-in scented oil dispensers. Similarly, all plug-in scented oil dispensers sold by S.C. Johnson & Son, Inc. ("S.C. Johnson") of Racine, Wis., generally only accept refills sold by S.C. Johnson under its Glade® brand and such refills are designed to only fit within S.C. Johnson plug-in scented oil dispensers. This is generally the case for most commercial plug-in scented oil dispensers and refills therefore. This can cause problems with the consumer, because consumers may forget the brand of dispenser they have and/or have multiple dispensers in their home and cannot recall which dispenser needs to be refilled and/or may prefer different scents, where one is only provided by one company and another is only provided by another company.

In recent years, attempts have been made to solve this problem for consumers. One such attempt that was made was to create a universal refill such that a single refill may interfit with housings of volatile material dispensers sold by multiple different companies under different brands. Such universal refills, however, often have complicated methods of insertion for different dispensers and can be confusing to the consumer, oftentimes leading to incorrect insertion of the refill. Such universal refills also may not provide the scents desired by the consumer.

Another attempt that has been made is to provide an adapter for a refill. The refill, without the adapter, is configured to be inserted into a first housing, but cannot be inserted into a second housing which has different dimensions than the first housing. The adaptor solves this problem by being secured to the refill and, thereafter, allowing for the refill having the adapter secured thereto, to be inserted into the second housing, but not the first housing. Such adaptors, however, can still cause confusion to the consumer and can be secured in an incorrect manner to the refills, again leading to incorrect insertion of the refill.

The present invention overcomes problems presented in the prior art and provides additional advantages over the prior art. Such advantages will become clear upon a reading of the attached specification in combination with a study of the drawings.

SUMMARY OF THE INVENTION

Briefly, a preferred embodiment of the present invention provides a volatile material dispenser comprising a housing and an implement which is operatively associated with the housing. The implement is configured to be movable between a first position and a second position, wherein the implement is configured to retain a first refill when the implement is in the first position, and wherein the implement is configured to retain a second refill when the implement is in the second position, and wherein the first and second refills have different features. The preferred embodiment may further comprise a heater disposed within the housing, whereby upon retainment of either the first or second refill, at least a portion of a wick of the first or second refill is disposed adjacent to the heater such that volatile material that moves through the wick is volatized by the heater. The preferred embodiment may further comprise a visual indicating system associated with at least one of the housing and the implement, wherein the visual indicating system provides an indication of whether the implement is positioned to retain the first refill or the second refill.

A preferred embodiment of the present invention provides a method of converting a volatile material dispenser for use between a first refill and a second refill, where the method comprises the steps of: (a) providing a volatile material dispenser having a housing and a refill retaining implement which is operatively associated with the housing; (b) providing first and second refills, wherein the first and second refills have different features; (c) positioning the refill retaining implement in a first position at which the refill retaining implement is configured to receive and retain the first refill; and (d) moving the refill retaining implement from the first position to a second position at which the refill retaining implement is configured to receive and retain the second refill.

A preferred embodiment of the present invention provides a method of retaining a refill in a volatile material dispenser, where the method comprises the steps of: (a) providing a volatile material dispenser having a housing and a refill retaining implement which is operatively associated with the housing; (b) providing a refill having a neck portion having a thread extending around an outer surface thereof; (c) inserting the refill into the housing of the volatile material dispenser; and (d) retaining the refill in position relative to the housing by engagement of the refill retaining implement with the thread of the neck portion of the refill.

BRIEF DESCRIPTION OF THE DRAWINGS

The organization and manner of the structure and operation of the invention, together with further objects and advantages thereof, may best be understood by reference to the following description, taken in connection with the accompanying drawings, wherein like reference numerals identify like elements in which.

DETAILED DESCRIPTION OF THE ILLUSTRATED EMBODIMENT

While the invention may be susceptible to embodiment in different forms, there is shown in the drawings, and herein will be described in detail, a specific embodiment with the understanding that the present disclosure is to be considered an exemplification of the principles of the invention, and is not intended to limit the invention to that as illustrated and described herein.

The invention provides a volatile material dispenser 100, as illustrated in FIGS. 1-10. In a preferred embodiment, the volatile material dispenser 100 is a plug-in scented oil dispenser. As will be described in further detail hereinbelow, the dispenser 100 is configured to receive and retain either a first refill 300 or a second refill 400, where the first and second refills 300, 400 have different features.

The first refill 300 is preferably a refill sold by S.C. Johnson & Son, Inc. ("S.C. Johnson") of Racine, Wis. under its Glade® brand, and such refills are purposely designed to only fit within S.C. Johnson plug-in scented oil dispensers. The first refill 300 is illustrated in FIGS. 11-14. The first refill 300 generally includes a container 302, a neck portion 304 extending upwardly from the container 302, a wick 306 in contact with a volatile material (not shown) in the container 302 and extending out of the neck portion 304, and a plug assembly 308 for holding the wick 306 within the neck portion 304. The container 302 includes a body 310 that is generally symmetrical about the neck portion 304 and includes opposing front and rear walls 312*a*, 312*b* and opposing side walls 314*a*, 314*b*. Protrusions (not shown) may extend outwardly from the front and rear walls 312*a*, 312*b*, respectively, and, in a present embodiment of the first refill 300, the protrusions are generally shell-shaped. The protrusions may alternatively have any other suitable shape. The neck portion 304 includes a thread 318 disposed on an outer surface thereof for attachment of a cap (not shown) thereto and the plug assembly 308 may include a sheath (not shown) extending upwardly therefrom, wherein the sheath surrounds at least a portion of the wick 306, leaving an upper portion 306*a* of the wick 306 exposed.

The second refill 400 is preferably a refill sold by Reckitt Benckiser ("Reckitt") of England under its Air Wick® brand, and such refills are purposely designed to only fit within Reckitt plug-in scented oil dispensers. The second refill 400 is illustrated in FIGS. 15-18. The second refill 400 generally includes a container 402, a neck portion 404 extending upwardly from the container 402, a wick 406 in contact with a volatile material (not shown) in the container 402 and extending out of the neck portion 404, and a plug assembly 408 for holding the wick 406 within the neck portion 404. The container 402 includes a body 410 that is generally asymmetrical about the neck portion 404 and includes front and rear walls 411, 413. The front wall 411 generally extends from a first end 415 of the rear wall 413 to a second end 417 of the rear wall 413 in a generally arcuate manner. From the first end 415 to the second end 417, the rear wall 413 has, in series, a first generally straight portion 419, a generally arcuate portion 421, and a second generally straight portion 423. The generally arcuate portion 421 generally bulges outwardly from the first and second generally straight portions 419, 423 in a direction opposite from a manner in which the front wall 411 bulges outwardly from the rear wall 413. The neck portion 404 includes an outwardly extending flange 416 provided at a base thereof and a thread 418 disposed on an outer surface thereof, above the flange 416, for attachment of a cap (not shown) thereto. The wick 406 has an exposed portion 406*a* extending upwardly from the neck portion 404.

As explained above, the first and second refills 300, 400 are each designed such that the refills 300, 400 will only be usable within a dispenser designed for that specific refill. Thus, a dispenser designed for the first refill 300 will receive and retain the first refill 300, but will not receive and retain the second refill 400. Likewise, a dispenser designed for the second refill 400 will receive and retain the second refill 400, but will not receive and retain the first refill 300. The reason for this is because each refill 300, 400 has its own features (which is understood to include dimensions, configurations, etc.), which only allow it to be used in its own respective dispenser. For instance, while each refill 300, 400 has an overall height H1, H2, respectively, that are generally equal to one another (it is to be understood that the drawings are not necessarily drawn to scale), the heights of the containers 302, 402, the neck portions 304, 404, and the wicks 306, 406 (the portions thereof which extend above the neck portions 304, 404) are different. More specifically, a height C1 of the container 302 of the first refill 300 is less than a height C2 of the container 402 of the second refill 400, a height N1 of the neck portion 304 of the first refill 300 is less than a height N2 of the neck portion 404 of the second refill 400, and a height W1 of the wick 306 of the first refill 300 (the portion thereof which extends above the neck portion 304) is greater than a height W2 of the wick 406 of the second refill 400 (which extends above the neck portion 404).

Despite the different features of the refills 300, 400, the present invention provides a dispenser 100 which is configurable to receive and retain either the first refill 300 or the second refill 400.

The dispenser 100 is best illustrated in FIGS. 1-10 and includes a housing 102, a refill retaining implement 104, a plug assembly 106, a heating assembly 108, and a wiring assembly 110.

Figure 2:
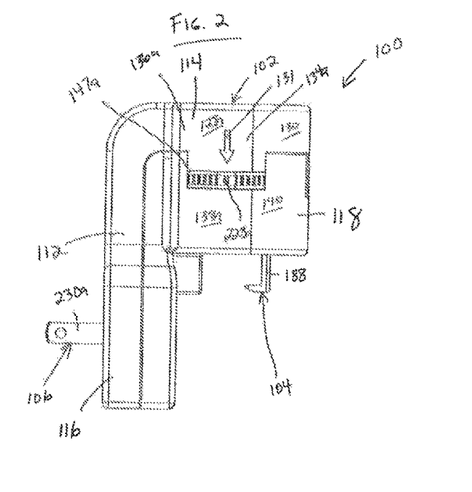
FIG. 2 is a side view of the volatile material dispenser illustrated in FIG. 1.
Figure 3:
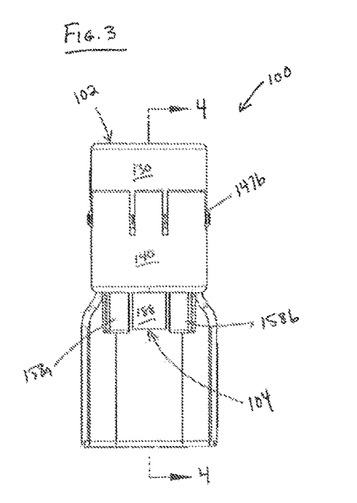
FIG. 3 is a front view of the volatile material dispenser illustrated in FIG. 1.
Figure 4:
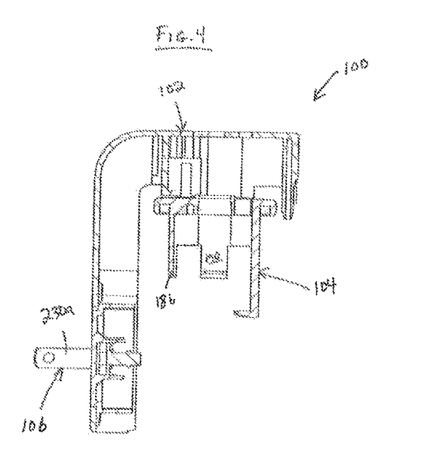
FIG. 4 is a cross-sectional view of the volatile material dispenser, taken along line 4-4 of FIG. 3.
Figure 5:
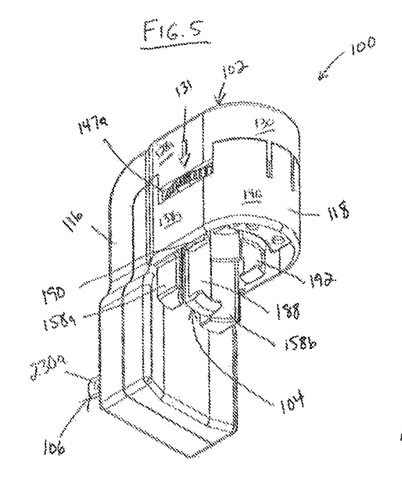
FIG. 5 is a perspective view of the preferred embodiment of the volatile material dispenser of the invention, which is configured to receive and retain a second refill.
Figure 6:
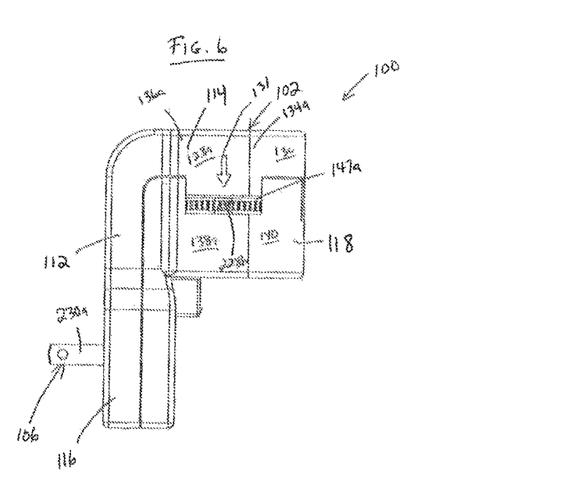
FIG. 6 is a side view of the volatile material dispenser illustrated in FIG. 5.
Figure 7:
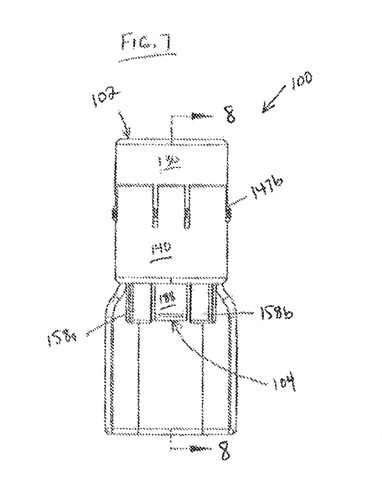
FIG. 7 is a front view of the volatile material dispenser illustrated in FIG. 5.
Figure 8:
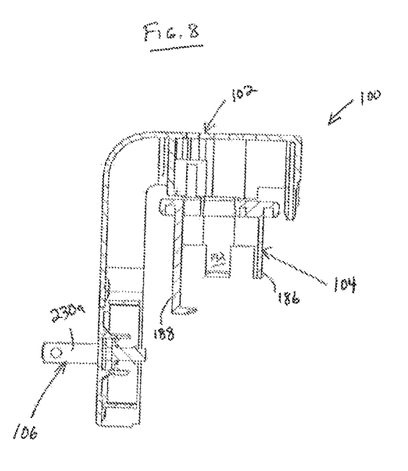
FIG. 8 is a cross-sectional view of the volatile material dispenser, taken along line 8-8 of FIG. 7.

As best illustrated in FIGS. 2 and 6, the housing 102 has a lower, generally vertical portion 112 and an upper, generally horizontal portion 114, such that the housing 102 is generally L-shaped in configuration. The housing 102 is preferably formed of a top housing portion 116, which is best illustrated in FIGS. 19-23, and a base housing portion 118, which is best illustrated in FIGS. 24-27. The top and base housing portions 116, 118 are secured together in an appropriate manner. In a preferred embodiment, the top housing portion 116 and the base housing portion 118 are preferably secured together at the lower, generally vertical portion 112 by at least one or more fasteners 120, and at the upper, generally horizontal portion 114 by interlocking parts. Further securement between the top and bottom housing portions 116, 118 could be provided by further fasteners, further interlocking parts, and/or adhesives, as desired.

At the upper, generally horizontal portion 114 of the housing 102, the top housing portion 116 has a top wall 126, first and second side walls 128*a*, 128*b* which extend downwardly from the top wall 126, and a front wall 130 which extends downwardly from the top wall 126 and which connects the first side wall 128*a* to the second side wall 128*b*. From the first side wall 128*a*, the front wall 130 preferably extends forwardly and then rearwardly in an arcuate, semi-circular manner, to the second side wall 128*b*. A plurality of apertures 132 are preferably provided through the top wall 126.

The first and second side walls 128*a*, 128*b* each have forward portions 134*a*, 134*b* and rearward portions 136*a*, 136*b*. The forward portions 134*a*, 134*b* of the first and second side walls 128*a*, 128*b* each extend farther downward from the top wall 126 than do the rearward portions 136*a*, 136*b* of the first and second side walls 128*a*, 128*b*. The front wall 130 extends downwardly from the top wall 126 preferably the same distance as do the rearward portions 136*a*, 136*b* of the first and second side walls 128*a*, 128*b*. An indicator 131 is provided on the forward portion 134*a* of the first side wall 128*a*. The indicator 131 is preferably in the form of a downwardly facing arrow.

At the upper, generally horizontal portion 114 of the housing 102, the base housing portion 118 has first and second generally vertical side walls 138*a*, 138*b*, and a generally vertical front wall 140 which connects the first side wall 138*a* to the second side wall 138*b*. From the first side wall 138*a*, the front wall 140 preferably extends forwardly and then rearwardly in an arcuate, semi-circular manner, to the second side wall 138b.

The first and second side walls 138a, 138b each have forward portions 142a, 142b and rearward portions 144a, 144b. The rearward portions 144a, 144b of the first and second side walls 138a, 138b each extend farther upward from a base edge 146 of the base housing portion 118 than do the forward portions 142a, 142b of the first and second side walls 138a, 138b. The front wall 140 extends upwardly from the base edge 146 preferably the same distance as to the rearward portions 144a, 144b of the first and second side walls 138a, 138b.

The configuration of the walls 128a, 128b, 130 of the top housing portion 116 are thus generally complementary to the configuration of the walls 138a, 138b, 140 of the base housing portion 118. When the top and base housing portions 116, 118 are secured together to form the housing 102, bottom edges of the rearward portions 136a, 136b of the first and second side walls 128a, 128b of the top housing portion 116 generally abut/seal against top edges of the rearward portions 144a, 144b of the first and second side walls 138a, 138b of the top housing portion 118, a bottom edge of the front wall 130 of the top housing portion 116 generally abuts/seals against a top edge of the front wall 140 of the base housing portion 118. Conversely, bottom edges of the forward portions 134a, 134b of the first and second side walls 128a, 128b of the top housing portion 116 do not abut/seal against top edges of the forward portions 142a, 142b of the first and second side walls 138a, 138b of the top housing portion 118, such that a pair of generally rectangular apertures 147a, 147b are provided through the upper, horizontal portion 114 of the housing 102. The indicator 131 is provided above the rectangular aperture 147a.

At the upper, generally horizontal portion 114 of the housing 102, the base housing portion 118 has a horizontal wall 148 which connects to the front wall 140 and the forward portions 142a, 142b of the first and second side walls 138a, 138b. The horizontal wall 148 is planar with the top edges of the forward portions 142a, 142b of the first and second side walls 138a, 138b. The horizontal wall 148 has a circular aperture 150 provided therethrough. A flange 152 extends upwardly from the horizontal wall 148 adjacent to the forwardmost portion of the circular aperture 150. The flange 152 does not extend as far upwardly as the top edges of the front wall 140 and the rearward portions 144a, 144b of the first and second side walls 138a, 138b.

A first arcuate wall 154 extends downwardly from the horizontal wall 148, is adjacent to the circular aperture 150, and is centered at the forwardmost portion of the circular aperture 150. The first arcuate wall 154 does not extend as far downwardly as do the front wall 140 and the first and second side walls 138a, 138b. The first arcuate wall 154 is further preferably connected to the front wall 140 for stability.

A second arcuate wall 156 extends downwardly from the horizontal wall 148, is adjacent to the circular aperture 150, and is centered at the rearwardmost portion of the circular aperture 150. The second arcuate wall 156 generally has an inverted U-shape such that it has a pair of legs 158a, 158b separated by a base 160. The base 160 does not extend as far downwardly as does the first arcuate wall 154, but the legs 158a, 158b extend further downwardly than do the front wall 140 and the first and second side walls 138a, 138b. For stability, the base 160 is further preferably connected to a front wall 162 of the base housing portion 118 provided at the lower, vertical portion 112 of the housing 102. Also for stability, the leg 158a is further preferably connected to the front wall 162 of the base housing portion 118 and the first side wall 138a, while the leg 158b is further preferably connected to the front wall 162 of the base housing portion 118 and the second side wall 138b. The arcuate walls 154, 156 serve a further purpose, as will be discussed in further detail hereinbelow.

The front wall 162 of the base housing portion 118 provides a center vertical portion 164 and opposite, side vertical portions 166a, 166b. The opposite, end vertical portions 166a, 166b are angled relative to the center vertical portion 164 such that the lower, vertical portion 112 of the housing 102 has a greater thickness at its ends as compared to its middle.

The refill retaining portion 104 is best illustrated in FIGS. 28-32. The refill retaining portion 104 has a top wall 168 which is generally circular in configuration. An outer cylindrical wall 170 extends downwardly from an outer edge of the top wall 168 to a bottom circular edge 172 of the outer cylindrical wall 170. An outer surface 174 of the outer cylindrical wall 170 preferably has a plurality of ribs or striations 176 provided thereon which assist in gripping the outer cylindrical wall 170, as will be discussed in further detail herein.

The refill retaining portion 104 has an inner wall 178 which extends downwardly from a lower surface of the top wall 168 to a bottom edge 180 of the inner wall 178. The bottom edge 180 of the inner wall 178 is positioned further from the top wall 168 than is the bottom circular edge 172 of the outer cylindrical wall 170. The inner wall 178 has an outer cylindrical surface 181 which is positioned inwardly from the outer cylindrical wall 170 such that a channel 182 is provided between the inner wall 178 and the outer cylindrical wall 170. A pair of generally oppositely positioned walls 184a, 184b span the channel 182 and connect the inner wall 178 to the outer cylindrical wall 170.

Four arms 186, 188, 190, 192 extend downwardly from the bottom edge 180 of the inner wall 178, and are each generally positioned approximately ninety degrees apart from an adjacent arm 186, 188, 190, 192. Each arm 186, 188, 190, 192 has an outer surface which is generally arcuate in configuration and which matches the arc of the outer cylindrical surface 181 of the inner wall 178 from which it extends. Arm 186 has an inner surface which is generally arcuate in configuration and which matches the arc of an inner cylindrical surface of the inner wall 178 from which it extends, however, each of arms 188, 190, 192 have inner surfaces which are generally planar in configuration. The inner planar surfaces 188, 190, 192 are extensions of inner planar surfaces of the inner wall 178, which extend upwardly to the top wall 168.

Arm 186 extends downwardly to a bottom edge 194 thereof. Arm 188 is positioned opposite arm 186 and extends downwardly to a bottom edge 196 thereof. The bottom edge 196 is positioned further downwardly from the bottom edge 180 than is the bottom edge 194. Arm 190 is positioned between arm 186 and arm 188 and extends downwardly to a bottom edge 198 thereof. Arm 192 is positioned between arm 186 and arm 188, and opposite of arm 190, and extends downwardly to a bottom edge 200 thereof. Bottom edges 194, 198, 200 are all generally planar with one another.

Arms 188, 190, 192 each have a flange 202, 204, 206, respectively, which extends inwardly proximate the bottom edges 196, 198, 200 thereof. Each flange 202, 204, 206, has a flat upper surface 208, 210, 212, and angled lower surface 214, 216, 218, and an arcuate inner edge 220, 222, 224.

Each of the arms 186, 188, 190, 192 may be slightly flexed inwardly or outwardly as desired/required.

The top wall 168 has an aperture 226 provided therethrough. The aperture 226 is preferably circular in configuration and is preferably centered between the inner wall 178.

The outer surface 174 of the outer cylindrical wall 170 is preferably provided with a pair of indicators 228a, 228b. Indicator 228a is generally in alignment with arm 190 while indicator 228b is generally in alignment with arm 192. For reasons which will become evident hereinbelow, indicator 228a is preferably the letter "G", while indicator 228b is preferably the letters "AW".

The refill retaining portion 104 may be provided with other cutouts or stabilizing features as are desired to either save costs on the materials used to form the refill retaining portion 104, or to provide further stabilization to parts of the refill retaining portion 104.

The refill retaining portion 104 is retained in position within the housing 102 between the top housing portion 116 and the base housing portion 118. The inner wall 178 of the refill retaining portion 104 is positioned through the circular aperture 150 of the horizontal wall 148 of the base housing portion 118. The cylindrical outer surface of the inner wall 178 is in opposing relationship with, and positioned slightly apart from, the first and second arcuate walls 154, 156 of the base housing portion 118. The flange 152 extends into the channel 182 of the refill retaining portion 104 and is preferably of a height such that the bottom circular edge 172 of the refill retaining portion 104 is slightly positioned above the horizontal wall 148 of the base housing portion 118.

When the top housing portion 116 and the bottom housing portion 118 are secured together to form the housing 102, portions of the outer cylindrical wall 170 of the refill retaining portion 104 extend through the rectangular apertures 147a, 147b, thereby allowing a user to move the outer cylindrical wall 170 in a rotatable manner, which is assisted by the plurality of ribs/striations 176 provided on the outer cylindrical wall 170 of the refill retaining portion 104.

Figure 9:
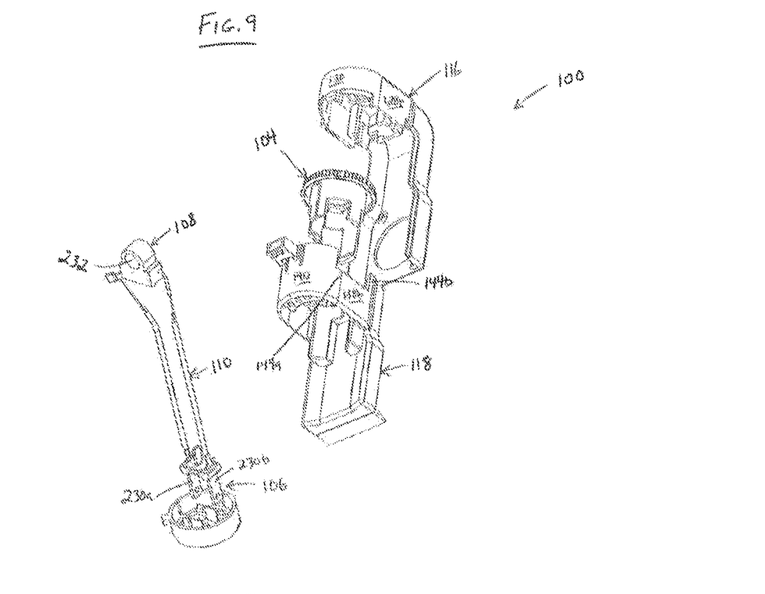
FIG. 9 is an exploded perspective view of the preferred embodiment of the volatile material dispenser of the invention, which is configured to receive and retain the second refill.
Figure 10:
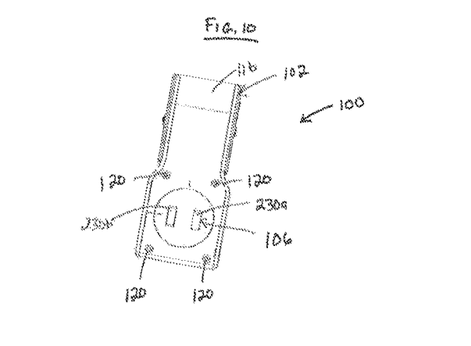
FIG. 10 is a rear view of the preferred embodiment of the volatile material dispenser.
Figure 11:
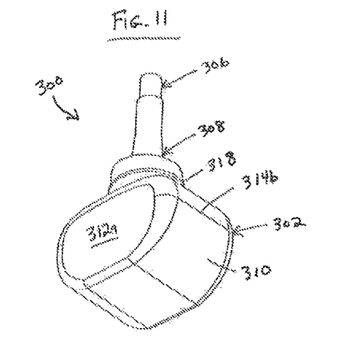
FIG. 11 is a perspective view of the first refill to be received and retained within the preferred embodiment of the volatile material dispenser of the invention.
Figure 12:
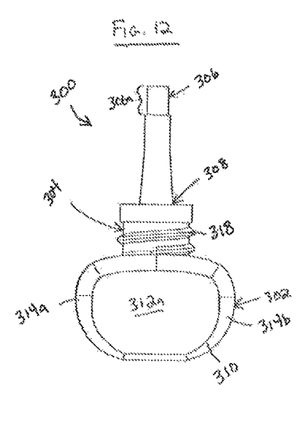
FIG. 12 is a front view of the first refill illustrated in FIG. 11.
Figure 13:
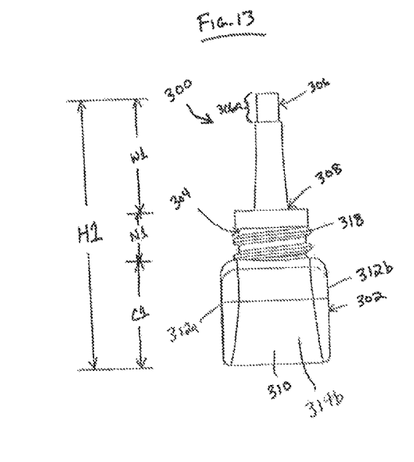
FIG. 13 is a side view of the first refill illustrated in FIG. 11.
Figure 14:
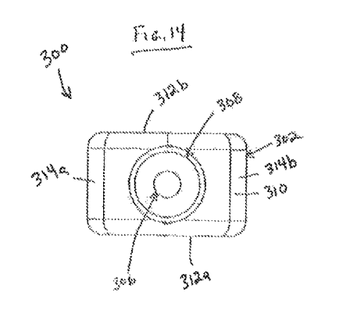
FIG. 14 is a top view of the first refill illustrated in FIG. 11.
Figure 15:
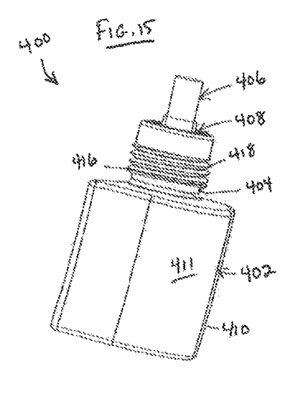
FIG. 15 is a perspective view of the second refill to be received and retained within the preferred embodiment of the volatile material dispenser of the invention.
Figure 16:
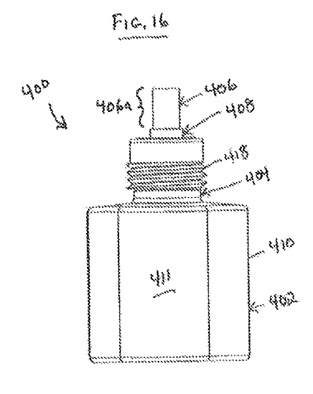
FIG. 16 is a front view of the second refill illustrated in FIG. 15.
Figure 17:
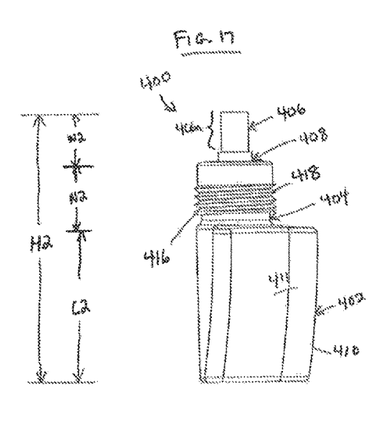
FIG. 17 is a side view of the second refill illustrated in FIG. 15.
Figure 18:
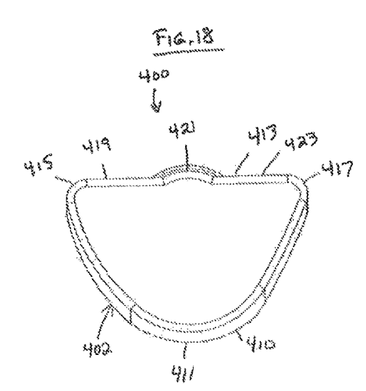
FIG. 18 is a bottom view of the second refill illustrated in FIG. 15.
Figure 19:
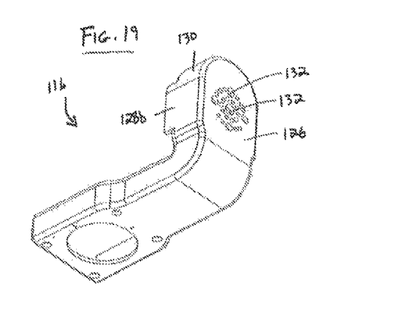
FIG. 19 is a perspective view of a top housing portion of a housing of the preferred embodiment of the volatile material dispenser of the invention.
Figure 20:
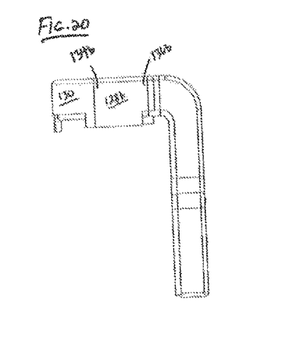
FIG. 20 is a side view of the top housing portion illustrated in FIG. 19.
Figure 21:
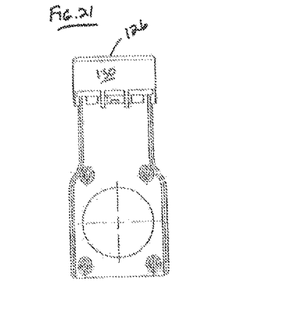
FIG. 21 is a front view of the top housing portion illustrated in FIG. 19.
Figure 22:
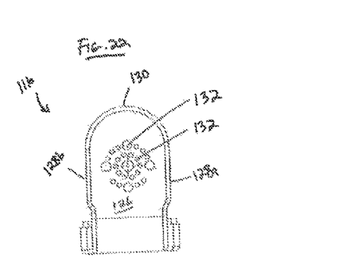
FIG. 22 is a top view of the top housing portion illustrated in FIG. 19.
Figure 23:
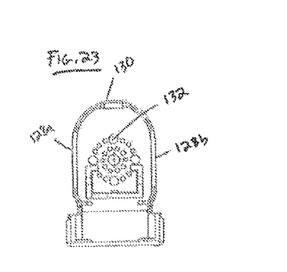
FIG. 23 is a bottom view of the top housing portion illustrated in FIG. 19.
Figure 24:
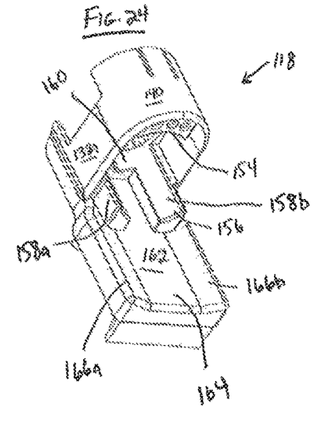
FIG. 24 is a perspective view of a base housing portion of the housing of the preferred embodiment of the volatile material dispenser of the invention.
Figure 25:
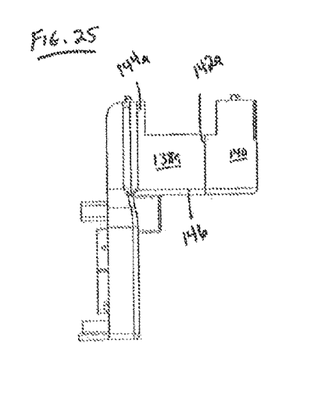
FIG. 25 is a side view of the base housing portion illustrated in FIG. 24.
Figure 26:
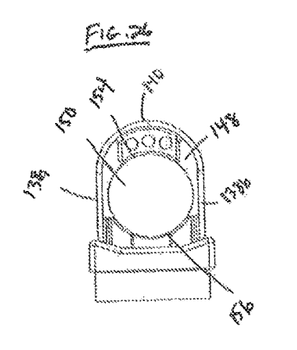
FIG. 26 is a bottom view of the base housing portion illustrated in FIG. 24.
Figure 27:
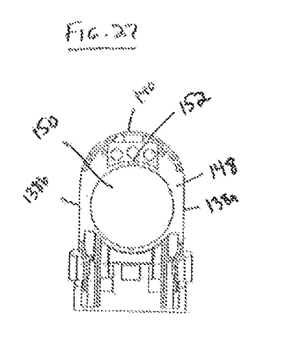
FIG. 27 is a top view of the base housing portion illustrated in FIG. 24.
Figure 28:
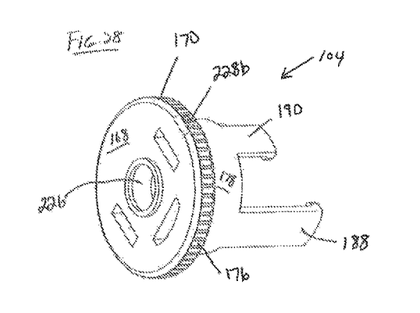
FIG. 28 is a perspective view of a refill retaining implement of the preferred embodiment of the volatile material dispenser of the invention.
Figure 29:
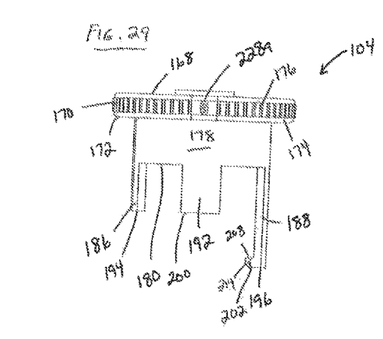
FIG. 29 is a side view of the refill retaining implement illustrated in FIG. 28.
Figure 30:
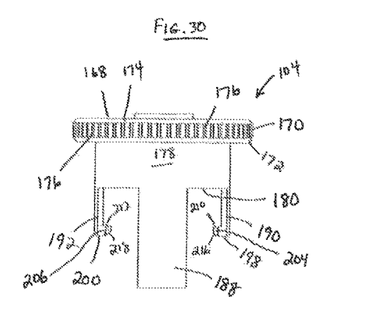
FIG. 30 is a front view of the refill retaining implement illustrated in FIG. 28.
Figure 31:
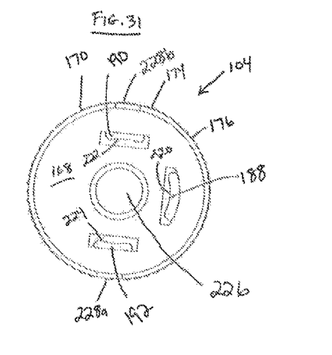
FIG. 31 is a top view of the refill retaining implement illustrated in FIG. 28.
Figure 32:
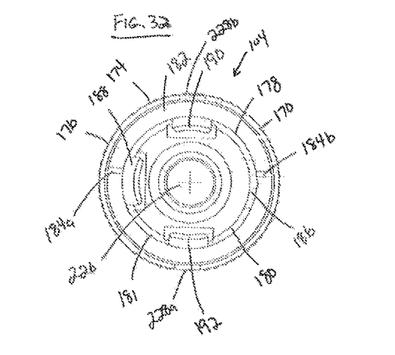
FIG. 32 is a bottom view of the refill retaining implement illustrated in FIG. 28.
Figure 33:
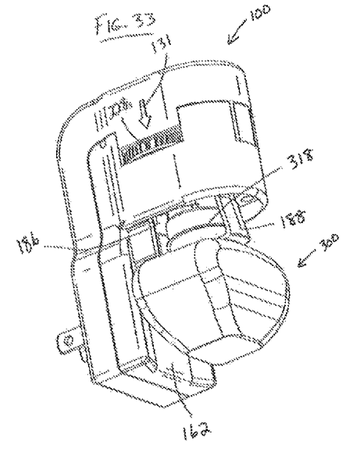
FIG. 33 is a perspective view of the preferred embodiment of the volatile material dispenser of the invention retaining the first refill.
Figure 34:
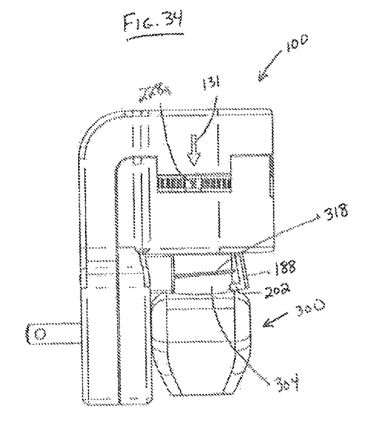
FIG. 34 is a side view of the preferred embodiment of the volatile material dispenser of the invention retaining the first refill.
Figure 35:
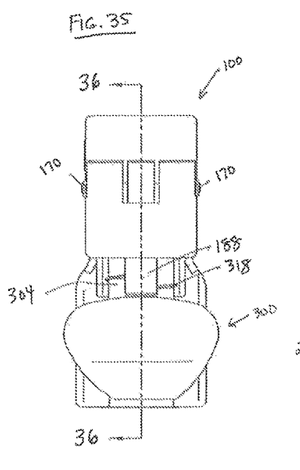
FIG. 35 is a front view of the preferred embodiment of the volatile material dispenser of the invention retaining the first refill.
Figure 36:
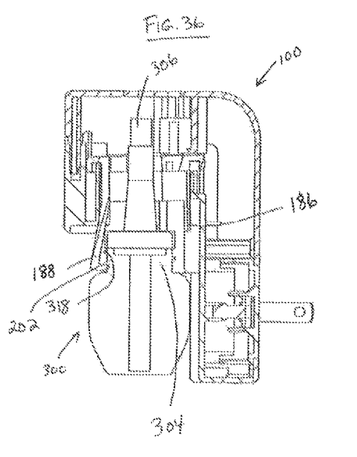
FIG. 36 is a cross-sectional view of the preferred embodiment of the volatile material dispenser of the invention retaining the first refill, taken along line 36-36 of FIG. 35.
Figure 37:
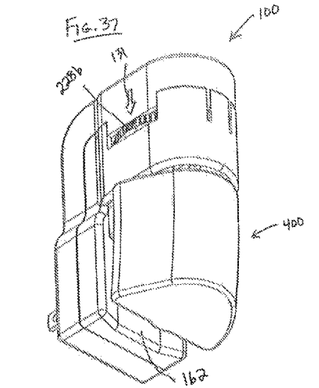
FIG. 37 is a perspective view of the preferred embodiment of the volatile material dispenser of the invention retaining the second refill.
Figure 38:
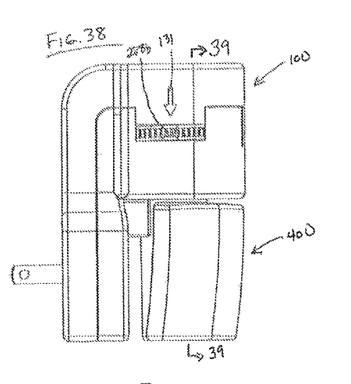
FIG. 38 is a side view of the preferred embodiment of the volatile material dispenser of the invention retaining the second refill.
Figures 39, 40, 41, 42:
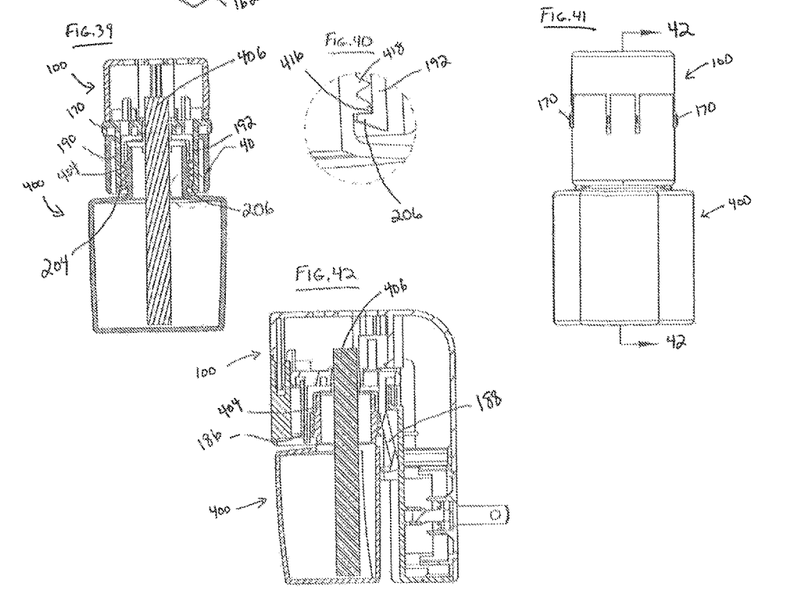
FIG. 39 is a cross-sectional view of the preferred embodiment of the volatile material dispenser of the invention retaining the second refill, taken along line 39-39 of FIG. 38.
FIG. 40 is an enlarged portion of the preferred embodiment of the volatile material dispenser of the invention retaining the second refill, taken from circle 40 of FIG. 39.
FIG. 41 is a front view of the preferred embodiment of the volatile material dispenser of the invention retaining the second refill.
FIG. 42 is a cross-sectional view of the preferred embodiment of the volatile material dispenser of the invention retaining the second refill, taken along line 42-42 of FIG. 41.

The plug assembly 106, which is best illustrated in FIG. 9, is generally retained within the lower, generally vertical portion 112 of the housing 102, preferably by structure provided by the base housing portion 118, but has a pair of plug prongs 230a, 230b which extend outwardly and rearwardly from the top housing portion 116. The plug assembly 106 is of a type which is well-known in the art and, therefore, detailed description of the structure and function of the plug assembly 106 will not be described herein. The plug assembly 106 is preferably an AC plug assembly and is preferably rotatable 90 degrees in order to allow for the prongs 230a, 230b of the dispenser 100 to be utilized in outlets having either vertical plug openings or horizontal plug openings. Of course, it is to be understood that other plug assemblies could be associated with the housing 102, as desired.

The heating assembly 108, which is best illustrated in FIG. 9, is generally retained within the upper, generally horizontal portion 114 of the housing 102, preferably by structure provided by the top housing portion 116. The heating assembly 108 has a generally vertical opening 232 provided therethrough which is sized and configured to receive either an exposed end of the wick 306 of the first refill 300, or an exposed end of the wick 406 of the second refill 406. The generally vertical opening 232 of the heating assembly 108 is positioned over and in general alignment with the aperture 226 provided through the top wall 168 of the refill retaining implement 104, and under the plurality of apertures 132 provided through the top wall 126 of the top housing portion 116 of the housing 102. The heating assembly 108 is of a type which is well-known in the art and, therefore, detailed description of the structure and function of the heating assembly 108 will not be described herein. Of course, it is to be understood that other heating assemblies could be associated with the housing 102, as desired.

Within the housing 102, the wiring assembly 110, which is best illustrated in FIG. 9, is connected at one end to the plug assembly 106 and at the other end to the heating assembly 108. The wiring assembly 110 thus supplies power from the plug assembly 106 to the heating assembly 108, thereby providing for power to be supplied to the heating assembly 108 when the plug assembly 106 is plugged into an appropriate power outlet.

A description of the operation of the dispenser 100 is provided hereinbelow with reference to FIGS. 1-8 and 33-42.

Attention is first directed to FIGS. 1-4 and 33-36 and use of the dispenser 100 with the first refill 300, which is preferably the refill sold under the Glade® brand. When it is desired to use the dispenser 100 with the first refill 300, the dispenser 100 must be configured to receive and retain the first refill 300.

Figure 1:
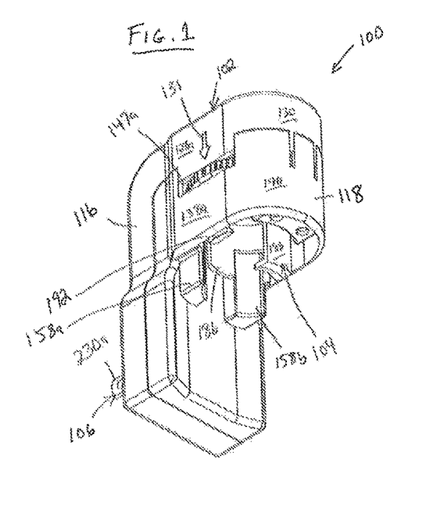
FIG. 1 is a perspective view of a preferred embodiment of a volatile material dispenser of the invention, which is configured to receive and retain a first refill.

In order to configure the dispenser 100 to receive and retain the first refill 300, the refill retaining portion 104 is manipulated to be moved into a first position. The refill retaining portion 104 is manipulated by moving the outer cylindrical wall 170 of the refill retaining portion 104, preferably in a clockwise rotatable manner, until the indicator 228a (e.g., the letter "G") is generally positioned below the indicator 131 (e.g., the arrow—with the arrow pointing to the letter "G"), as best illustrated in FIGS. 1 and 2. The plurality of ribs/striations 176 on the outer cylindrical wall 170 assist a user in gripping/moving the refill retaining portion 104. The portions of the outer cylindrical wall 170 that extend through the rectangular apertures 147a, 147b of the housing 102 are the portions which preferably allow for the outer cylindrical wall 170 to be gripped/moved. Once the indicators 228a, 131 are in general alignment, further clockwise movement of the refill retaining portion 104 is prevented by the flange 152 abutting against the wall 184a spanning the channel 182 defined by the refill retaining implement 104.

When the indicators 228a, 131 are in general alignment, the arm 188 is positioned in a forward position such that it is adjacent to the first arcuate wall 154, and the arm 186 is positioned in a rearward position such that is adjacent to the second arcuate wall 156 and generally positioned between the legs 158a, 158b, as illustrated in FIGS. 1-4.

The first refill 300, with the cap removed, is then inserted into the dispenser 100, with the rear wall 312b of the first refill 300 facing the front wall 162 of the base housing portion 118. The upper exposed portion 306a of the wick 306 is inserted upwardly between the arms 186, 188, 190, 192, between the inner surface of the inner wall 178, through the aperture 226 of the top wall 168, and into the vertical opening 232 of the heating assembly 108. In order to move the wick 306 into this position, one or more of the arms 186, 188, 190, 192 may be flexed outwardly as necessary, but preferably only the arm 188 is flexed outwardly in order to accommodate the neck portion 304 of the first refill 300. The arm 188 may be directly flexed outwardly, or may be flexed outwardly by upward movement of the first refill 300 relative to the housing 102.

When the wick 306 of the first refill 300 is properly positioned, the flange 202 of the arm 188 is flexed inwardly until the arcuate inner edge 220 of the flange 202 is generally positioned against the neck portion 304 of the first refill 300, with the flat upper surface 214 of the flange 202 being positioned below the thread 318 of the first refill 300, as best illustrated in FIGS. 33-36. Thus, the flange 202 of the arm 188 of the refill retaining implement 104, acting to return to its normal position (a non-flexed state) supports and retains the first refill 300 in position. In the preferred embodiment, the arms 186, 190, 192 of the refill retaining implement 104 do not act to support or retain the first refill 300 in position.

If a protrusion is provided on the rear wall 312b of the first refill 300, the recessed center vertical portion 164 of the front wall 162 of the base housing portion 118 accommodates the protrusion. Regardless, the side vertical portions 166a, 166b of the front wall 162 of the base housing portion 118 are preferably in abutment with the rear wall 312b of the first refill 300, to provide further stability to the first refill 300 while retained in position in the dispenser 100. The legs 158a, 158b of the second arcuate wall 156 of the base housing portion 118 further prevent upward movement of the first refill 300. A bottom of the container 302 of the first refill 300 preferably does not extend below a bottom of the housing 102 of the dispenser 100.

Once the first refill 300 is empty, the first refill 300 can be removed from the dispenser 100, preferably by flexing the arm 188 outwardly, thereby removing the flange 202 from engagement with the thread 318 on the neck portion 304 of the refill 300. The arm 188 can be flexed outwardly either by directly moving the arm 188, and/or by pulling downward on the first refill 300 which causes the arm 188 to flex outwardly. The first refill 300 can then be removed from the dispenser 100 and a new first refill 300 can be inserted and retained within the dispenser 100 as discussed above. Alternatively, if the second refill 400 is to be inserted and retained within the dispenser 100 after removal of the first refill 300, the dispenser 100 can be adjusted to a position configured to receive the second refill 400.

Attention is now directed to FIGS. 5-8 and 37-42 and use of the dispenser 100 with the second refill 400, which is preferably the refill sold under the Air Wick® brand. When it is desired to use the dispenser 100 with the second refill 400, the dispenser 100 must be configured to receive and retain the second refill 400.

In order to configure the dispenser 100 to receive and retain the second refill 400, the refill retaining portion 104 is manipulated to be moved into a second position. The refill retaining portion 104 is manipulated by moving the outer cylindrical wall 170 of the refill retaining portion 104, preferably in a counter-clockwise rotatable manner, until the indicator 228b (e.g., the letters "AW") is generally positioned below the indicator 131 (e.g., the arrow—with the arrow pointing to the letters "AW"), as best illustrated in FIGS. 5-8. The plurality of ribs/striations 176 on the outer cylindrical wall 170 assist a user in gripping/moving the refill retaining portion 104. The portions of the outer cylindrical wall 170 that extend through the rectangular apertures 147a, 147b of the housing 102 are the portions which preferably allow for the outer cylindrical wall 170 to be gripped/moved. Once the indicators 228b, 131 are in general alignment, further counter-clockwise movement of the refill retaining portion 104 is prevented by the flange 152 abutting against the wall 184b spanning the channel 182 defined by the refill retaining implement 104.

When the indicators 228b, 131 are in general alignment, the arm 188 is positioned in a rearward position such that it is adjacent to the second arcuate wall 156 and generally positioned between the legs 158a, 158b, and the arm 186 is positioned in a forward position such that is adjacent to the first arcuate wall 154, as illustrated in FIGS. 5-8.

The second refill 400, with the cap removed, is then inserted into the dispenser 100, with the rear wall 413 of the second refill 400 facing the front wall 162 of the base housing portion 118. The upper exposed portion 406a of the wick 406 is inserted upwardly between the arms 186, 188, 190, 192, between the inner surface of the inner wall 178, through the aperture 226 of the top wall 168, and into the vertical opening 232 of the heating assembly 108. In order to move the wick 406 into this position, one or more of the arms 186, 188, 190, 192 may be flexed outwardly as necessary, but preferably the arms 188, 190, 192 are each flexed outwardly in order to accommodate the neck portion 404 of the second refill 400. The arms 188, 190, 192 may be directly flexed outwardly, or may be flexed outwardly by upward movement of the second refill 400 relative to the housing 102.

When the wick 406 of the second refill 400 is properly positioned, the flanges 204, 206 of the arms 190, 192 are flexed inwardly until the arcuate inner edges 222, 224 of the flange 204, 206 are generally positioned under the flange 416 of the neck portion 404 of the second refill 400, with the flat upper surfaces 216, 218 of the flanges 204, 206 being positioned below the flange 416, on opposite sides of one another, of the second refill 400. Thus, the flanges 204, 206 of the arms 190, 192 of the refill retaining implement 104, acting to return to their normal positions (a non-flexed state), support and retain the second refill 400 in position.

When the wick 406 of the second refill 400 is properly position, the arm 188 is in an outwardly flexed position with the arcuate inner edge 220 of the flange 220 of the arm 188 being positioned against the arcuate portion 421 of the rear wall 413 of the second refill 400, thereby providing further stability to the retainment of the second refill 400 in the dispenser 100. The arm 188 can be flexed outwardly to such a position in view of the opening provided between the legs 158a, 158b of the second arcuate wall 156 of the base housing portion 118. In the preferred embodiment, the arm 186 of the refill retaining implement 104 does not act to support or retain the second refill 400 in position.

The recessed center vertical portion 164 of the front wall 162 of the base housing portion 118 accommodates the arcuate portion 421 of the rear wall 413 of the second refill 400. The side vertical portions 166a, 166b of the front wall 162 of the base housing portion 118 are preferably in abutment with the first and second straight portions 419, 423 of the rear wall 413 of the second refill 400, to provide further stability to the second refill 400 while retained in position in the dispenser 100. A bottom of the container 402 of the second refill 400 preferably does not extend below a bottom of the housing 102 of the dispenser 100.

Once the second refill 400 is empty, the second refill 400 can be removed from the dispenser 100, preferably by flexing at least one of the arms 190, 192 outwardly, thereby removing the flanges 204, 206 from engagement with the thread 418 on the neck portion 404 of the refill 400. The arms 190, 192 can be flexed outwardly by directly moving the arms 190, 192, and/or the arms 190, 192 can be flexed outwardly by pulling downward on the second refill 400 relative to the housing 102. The second refill 400 can then be removed from the dispenser 100 and a new second refill 400 can be inserted and retained within the dispenser 100 as discussed above. Alternatively, if the first refill 300 is to be inserted and retained within the dispenser 100 after removal of the second refill 400, the dispenser 100 can be adjusted to a position configured to receive the first refill 300.

The indicators 131, 228a, 228b collectively form a visual indicating system of the dispenser 100.

The dispenser 100 thus may be used with either with the first refill 300 or the second refill 400, with a simple adjustment mechanism, namely the refill retaining implement 104. It is to be understood that, while the refill retaining implement 104 is described and illustrated as being used with either a first refill 300 or a second refill 400, that different refills may be able to be used with the refill retaining implement 104. Further, the refill retaining implement 104 could be configured to be adjustable between three or more positions to accommodate the use of three or more different types of refills.

While a preferred embodiment of the present invention is shown and described, it is envisioned that those skilled in the art may devise various modifications of the present invention without departing from the spirit and scope of the invention.

The invention claimed is:

1. A volatile material dispenser comprising:
 a housing comprising a top housing portion and a base housing portion, the base housing portion comprising a front wall, a base edge, and a leg; and
 a refill retaining implement retained between the top housing portion and the base housing portion, the refill retaining implement comprising an arm that extends below the base edge;
 wherein the refill retaining implement is rotatable relative to the housing between first and second positions;
 wherein when the refill retaining implement is in the first position, the arm is in a forward position adjacent to the front wall and opposite to the leg, such that the refill retaining implement is thereby configured to retain a first refill positioned between the arm and the leg; and
 wherein when the refill retaining implement is in the second position, the arm is in a rearward position adjacent to the leg and opposite to the front wall, wherein the refill retaining implement is thereby configured to retain a second refill.

2. The volatile material dispenser as defined in claim 1, further comprising a visual indicating system associated with at least one of the housing and the refill retaining implement, wherein the visual indicating system provides an indication of whether the refill retaining implement is in the first position or in the second position.

3. The volatile material dispenser as defined in claim 2, wherein the visual indicating system includes an arrow provided on the housing and first and second symbols provided on the refill retaining implement, wherein when the arrow is in general alignment with the first symbol, the visual indicating system provides an indication that the refill retaining implement is in the first position, and when the arrow is in general alignment with the second symbol, the visual indicating system provides an indication that the refill retaining implement is in the second position.

4. The volatile material dispenser as defined in claim 1, wherein the volatile material dispenser is a plug-in scented oil dispenser and wherein the housing has a heater disposed therein, whereby upon retainment of either the first or second refill, at least a portion of a wick of the first or second refill is disposed adjacent to the heater such that volatile material that moves through the wick is volatilized by the heater.

5. The volatile material dispenser as defined in claim 1, wherein the arm is a first arm and the volatile material dispenser further comprises second and third downwardly extending arms, the first arm extending further downwardly than the second and third arms.

6. The volatile material dispenser as defined in claim 5, wherein each of the first, second, and third arms has an inwardly extending flange, wherein the inwardly extending flanges of the first, second, and third arms are configured to engage at least one of the first and second refills in order to retain one of the first and second refills in position relative to the housing.

7. The volatile material dispenser as defined in claim 6, wherein each of the inwardly extending flanges has a lower angled surface and an upper horizontal surface.

8. The volatile material dispenser as defined in claim 5, wherein first arm is configured to engage a thread on a neck portion of the first refill and the second and third arms are configured to engage a flange on a neck portion of the second refill.

9. The volatile material dispenser as defined in claim 6, wherein each of the inwardly extending flanges are configured to be flexed outwardly in order to assist the dispenser in receiving one of the first and second refills to be retained in the dispenser.

10. The volatile material dispenser as defined in claim 5, wherein the first and second arms are positioned opposite one another, and wherein the third arm is positioned equidistantly between the first and second arms.

11. The volatile material dispenser as defined in claim 10, wherein the first arm is positioned forward of the second and third arms when the refill retaining implement is in the first position, and wherein the first arm is positioned rearward of the second and third arms when the refill retaining implement is in the second position.

12. The volatile material dispenser as defined in claim 1, wherein the refill retaining implement rotates approximately 180 degrees from the first position to the second position.

13. The volatile material dispenser as defined in claim 1, further comprising at least a pair of legs separated by a space, wherein when the refill retaining implement is in the second position, the arm is positioned between the pair of legs and configured to flex rearwardly into the space.

14. A method of converting a volatile material dispenser for use between a first refill and a second refill, wherein the method comprises the steps of:
 a) providing a volatile material dispenser housing comprising a top housing portion and a base housing portion, the base housing portion comprising a front wall, a base edge, and a leg;
 b) retaining a refill retaining implement between the top housing portion and the base housing portion, the refill retaining implement being rotatable relative to the housing and comprising an arm that extends below the base edge;
 c) positioning the refill retaining implement in a first position at which the refill retaining implement is configured to receive and retain the first refill positioned between the arm and the leg; and
 d) rotating the refill retaining implement relative to the housing from the first position to a second position at which the arm is adjacent to the leg and opposite to the front wall, and the refill retaining implement is configured to receive and retain the second refill.

15. The method as defined in claim 14, further comprising the step of rotating the refill retaining implement from the second position to the first position.

16. The method as defined in claim 14, wherein the volatile material dispenser has a visual indicating system which confirms the positioning of the refill retaining implement between the first and second positions.

17. The method as defined in claim 16, wherein the volatile material dispenser includes a single indicator on the housing and first and second indicators on the refill retaining implement, wherein alignment of the indicator on the housing with the first indicator on the refill retaining implement confirms the positioning of the refill retaining implement in the first position, and wherein alignment of the indicator on the housing with the second indicator on the refill retaining implement confirms the positioning of the refill retaining implement in the second position.

18. A volatile material dispenser comprising:
- a housing comprising a top housing portion and a base housing portion, the base housing portion comprising a front wall and a leg; and
- a refill retaining implement retained between the top housing portion and the base housing portion, the refill retaining implement comprising a plurality of arms, wherein a first arm is longer than the other arms;
- wherein the refill retaining implement is rotatable relative to the housing between first and second positions;
- wherein when the refill retaining implement is in the first position, the first arm is in a forward position adjacent to the front wall and opposite to the leg, such that the refill retaining implement is thereby configured to retain a first refill positioned between the first arm and the leg; and
- wherein when the refill retaining implement is in the second position, the first arm is in a rearward position adjacent to the leg and opposite to the front wall, wherein the refill retaining implement is thereby configured to retain a second refill.

19. The volatile material dispenser as defined in claim 18, wherein the volatile material dispenser is a plug-in scented oil dispenser and wherein the housing has a heater disposed therein, whereby upon retainment of either the first or second refill, at least a portion of a wick of the first or second refill is disposed adjacent to the heater such that volatile material that moves through the wick is volatilized by the heater.

20. The volatile material dispenser as defined in claim 18, the dispenser further comprising a second arm and a third arm, wherein first arm is configured to engage a thread on a neck portion of the first refill and the second and third arms are configured to engage a flange on a neck portion of the second refill.

* * * * *